United States Patent [19]

James

[11] Patent Number: 4,752,690

[45] Date of Patent: Jun. 21, 1988

[54] METHOD AND APPARATUS FOR DETECTING INCONGRUITIES, SUCH AS AIR BUBBLES, IN FLUID MATERIAL

[75] Inventor: Bobby D. James, Hialeah, Fla.

[73] Assignee: Coulter Electronics, Inc., Hialeah, Fla.

[21] Appl. No.: 895,117

[22] Filed: Aug. 11, 1986

[51] Int. Cl.$^4$ .................. G01N 21/59; G01N 21/85
[52] U.S. Cl. ................................ 250/349; 250/341; 250/356.1; 250/564
[58] Field of Search ............... 250/357.1, 356.1, 345, 250/349, 341, 573, 576, 564; 356/436; 364/416

[56] References Cited

U.S. PATENT DOCUMENTS

| | | | |
|---|---|---|---|
| 3,549,994 | 12/1970 | Rothermel et al. | 324/71.1 |
| 3,680,962 | 8/1972 | Hayakawa | 356/338 |
| 4,152,391 | 5/1979 | Cabrera | 422/103 |
| 4,210,809 | 7/1980 | Pelavin | 250/343 |
| 4,280,495 | 7/1981 | Lampert | 604/4 |
| 4,312,341 | 1/1982 | Zissimopoulos et al. | 604/67 |
| 4,344,429 | 8/1982 | Gupton et al. | 604/67 |
| 4,366,384 | 12/1982 | Jensen | 250/575 |
| 4,371,786 | 2/1983 | Kramer | 250/343 |
| 4,418,565 | 12/1983 | St. John | 73/19 |

FOREIGN PATENT DOCUMENTS

| | | | |
|---|---|---|---|
| 0109198 | 5/1984 | European Pat. Off. | 250/356.1 |
| 3343598 | 6/1985 | Fed. Rep. of Germany | 250/573 |
| 84/01588 | 2/1984 | PCT Int'l Appl. | |

Primary Examiner—Janice A. Howell
Assistant Examiner—Constantine Hannaher
Attorney, Agent, or Firm—Carl Fissell, Jr.; Gerald R. Hibnick

[57] ABSTRACT

Apparatus for detecting contaminants, including emboli, in a blood sample prior to blood cell analysis, wherein fluid density sensors are arranged on opposite sides of a fluid segmenting valve to provide electrical signals indicative of the degree of optical opacity of the fluid flowing through the sensors. The derived signals are compared against a diluent reference level signal to provide resultant signal outputs indicating the presence or absence of emboili or other contaminants within the segmented portion of fluid.

11 Claims, 6 Drawing Sheets

METHOD AND APPARATUS FOR DETECTING INCONGRUITIES, SUCH AS AIR BUBBLES, IN FLUID MATERIAL

BACKGROUND OF THE INVENTION

1. Field of the Invention

The present invention relates to hematology analyzers and to analyzers of the fully automated type which require little or no operational "hands on" activity by attendant operators.

More particularly, the invention has to do with automatic means and method for monitoring human blood samples and detecting the presence of contaminants therein, such as air bubbles, etc.

2. Description of the Prior Art

A wide variety of mechanisms and apparatuses have been suggested and patented for detecting contaminants in fluid flow, such as air bubbles in blood flow hematology apparatuses.

U.S. Pat. No. 4,280,495, entitled "Air Emboli Detection", describes and claims a method and apparatus for use in cardiopulmonary bypass surgery wherein a modular sensor is adapted to releasably clamp a blood flow tubing in a vertical orientation below, and includes an LED infrared source and a photodetector. Pulsed power is applied to the light source only at preselected periodic intervals for removing power to a blood pump when emboli are detected.

This construction is quite dissimilar to that of the present application.

U.S. Pat. No. 4,312,341, entitled "Bubble Detector", describes a flow metering apparatus for detecting bubble formation in tubing subject to deformation from internal fluid pressure, wherein a light detector is positioned on the opposite side of the tubing from a light source, such that light transmitted through the tubing to the detector is dependent on the presence of fluid in the tubing and the shape of the lumen of the tubing. Control means interrupts the fluid flow when received light falls below a predetermined level. Tubing deformation due to pressure changes in the fluid are prevented by forming members surrounding the tubing.

The described arrangement differs quite measurably from Applicant's claimed combination.

In U.S. Pat. No. 4,344,429, entitled "Bubble Detector with Feedback Circuit for Improved Sensitivity", there is described and illustrated a flow metering apparatus for use with transparent tubing utilizing the lens effect of fluid within the lumen of the tubing to detect the presence of fluid within the tubing. A single light source is positioned on one side of the tubing and two angularly displaced light detectors are placed on the opposite side of the tubing. The variation in intensity of the detected light due to the presence of or absence of fluid is an indication of a bubble in the system.

Applicant's structural combination is completely different than this arrangement.

U.S. Pat. No. 4,371,786, entitled "Method and Apparatus for Detecting Bubbles in a Liquid" relates to: A method and apparatus for sensing the presence of bubbles in a liquid wherein radiation is directed through said liquid toward a radiation responsive sensor and the differential between the response of the sensor when a bubble is not present in the radiation path and the response thereof when a bubble is present in the radiation path is markedly increased by limitation of the radiation which can reach said sensor to wavelengths strongly absorbed by said liquid.

As with the preceding patented apparatus, Applicant's bubble detection mechanism and method are quite different from the foregoing.

The "Air Bubble Detector" of U.S. Pat. No. 4,366,384 describes an apparatus in which multiple pairs of light sensors are positioned along a transparent pipe, such that light is directed to one sensor of each pair while light is reflected to the other sensor of each pair. The reflective sensor of each pair is positioned midway between a light source and its associated direct light receiving sensor. The outputs of the two light sensors are fed into a logic circuit, which produces one output when the light levels seen by the two sensors are generally alike, and another output when they are substantially different. If a bubble is present, both sensors see a high light level.

The dual sensor bubble detector apparatus of the present application is markedly different from the apparatus hereinabove described, both in function and construction.

"Contaminant Detector Comprising Means for Selectively Applying Pressure to Liquify Bubbles", as described in U.S. Pat. No. 3,680,962, relates to an apparatus in which a rigid metal tube open at opposite ends is provided with an angularly disposed branch tube integral therewith. A light source is disposed at one end of the tube and a first photo-optical sensor is placed at its opposite end. A second photo-optical sensor is positioned at the open end of the branch tube, with liquid contained in the tube having contaminants therein. Light is scattered and absorbed by the contaminants, so that a reduced amount of light is received by the first sensor as compared with a contaminant free liquid, which provides a greater resistance value at the first sensor. In contrast, the light scattered by the contaminants in the branch tube decreases the second sensor's resistance value. By means of an operably coupled bridge circuit, the variation in resistance values of the first and second sensors can be converted into a variation of light intensity, so as to detect contamination or a clear tube.

This is completely dissimilar to Applicant's method and apparatus as set forth in the Specification hereinafter.

A U.S. Pat. No. 4,418,565, entitled "Ultrasonic Bubble Detector", describes a rigid housing of glass-filled polytetrafluoroethylene having a channel in this one-piece housing for receiving flow tubing in which bubbles are detected. A first ultrasonic sending transducer means is positioned in the housing on one side of the channel. A second ultrasonic receiving transducer means is positioned on the other side of the channel, the sending and receiving transducer means being of the type for respectively sending and receiving ultrasound energy at a frequency of 1 to 3 megahertz. The presence of a bubble significantly alters the transmission of ultrasound energy. This alteration is electronically detected.

This construction is in complete contrast to the simplified bubble sensor arrangement of Applicant's application.

SUMMARY OF THE INVENTION

The present invention is an innovative and inventive modification for use, for example, in the COULTER COUNTER ® STKR analyzer described and claimed in PCT/US84/01588, International Publication No.

WO85/01797, International Publication Date 25 Apr. 1985 (25.04.85). Such apparatus is characterized as a "walk-away" system in that, once it is loaded with cassettes of the sample tubes for testing, the operator can walk away to perform some other task, without concern for the analyzer operation, which will perform its various functions unattended.

The Bubble/Blood detector of the present invention includes a novel arrangement of parts that monitors the blood flow for contamination, through novel optical sensing members positioned at the input and output sides of the analyzer's sample segmenting and diluting valve. An isotonic diluent, such as ISOTON ® III, is employable as the blood diluent and electrolyte. The detector checks the diluent in the input and output tubing to the sample valve to see if it is the same at the beginning of the cycle. It checks to see that no bubbles larger than 0.060 microliter get past the input side sensor during the aspiration of the whole blood from the sample tube. It also checks the blood on the input and output tubing to and from the sample valve to see if it is the same at the time the valve "segments" a microliter amount of the sample, i.e., forwards an aliquot of the sample for analysis to the transducer "bath".

A fixed volume (175 µL—one hundred seventy five microliters) of material to be tested, i.e., blood, is aspirated from each tube of blood. The sample valve segments out a portion of the volume (for WBC—white blood count and RBC—red blood count). These portions are sent to the red and white transducer containing baths for dilution with the diluent-electrolyte. For example, the segmented volume of blood for the RBC dilution is 1.6 µL. If a bubble of 0.1 µL displaced that much blood, then the dilution for RBC would be in error by 6%. This error would be "flagged"—indicated—to the operator by display and printout.

The two sensors of the detector are connected to an electronic circuit that basically consists of two adjustable feedback voltage regulators, two amplifiers, two sample and hold circuits, one difference amplifier, one adder, one inverter, four comparators, and a seven state controller with logic. There are three signals needed for inputs ("Reference Sense", "Blood Flow", and "Blood Sense"). These signals come from the main controller of the analyzer, which is not otherwise described herein.

There are also four output signals from the controller and logic that indicate failed conditions. Two outputs indicate, respectively, that (1) the diluent, at the beginning of the cycle, or (2) the blood, at the segmenting time of the cycle was not the same at the front and rear of the sample valve. Another output (3) indicates that the preset threshold level (80% down from reference level) was not exceeded. An output fail condition (4) indicates that a bubble was detected during aspiration. These four signals are sent to the main system controller of the analyzer for processing.

Other objects, features, and advantages of the invention will become apparent as the description proceeds, reference being had to the accompanying drawings.

BRIEF DESCRIPTION OF THE THE DRAWINGS

FIG. 2A is an enlarged, schematic view of the present invention as associated with the aspirating needle, the COULTER ® segmenting valve, and the aspiration pump;

FIG. 4A is a block diagram of a computer implementation for the present inventive apparatus;

DESCRIPTION OF THE PREFERRED EMBODIMENT OF THE INVENTION

1. Functional Description

Figure 1:
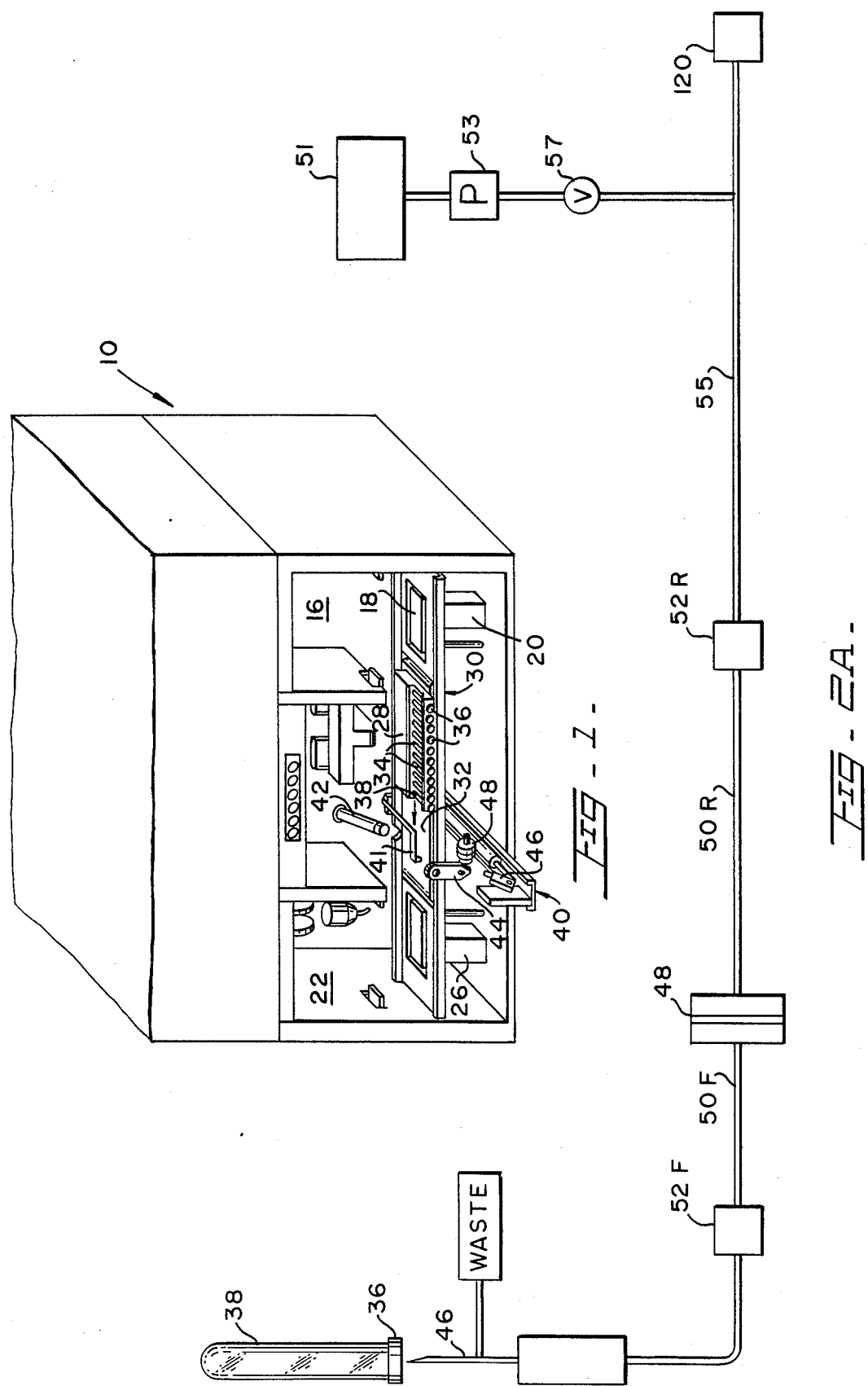
FIG. 1 is a perspective, somewhat pictorial view, of a hematology analyzer with the automatic handling features displayed.

By way of background only, and with reference to FIG. 1, there is shown, somewhat pictorially, the entire hematology analyzer 10 which preferably is of the COULTER COUNTER ® Model S Plus STKR type, but that is not an essential limitation. The analyzer 10 has full capabilities for accomplishing multiparameter hematology analysis from whole blood samples. It contains the electronic, pneumatic, and fluid moving components, generally taught in U.S. Pat. No. 3,549,994, as well as state of the art improvements, including, but not limited to, microprocessor control.

Figure 2:
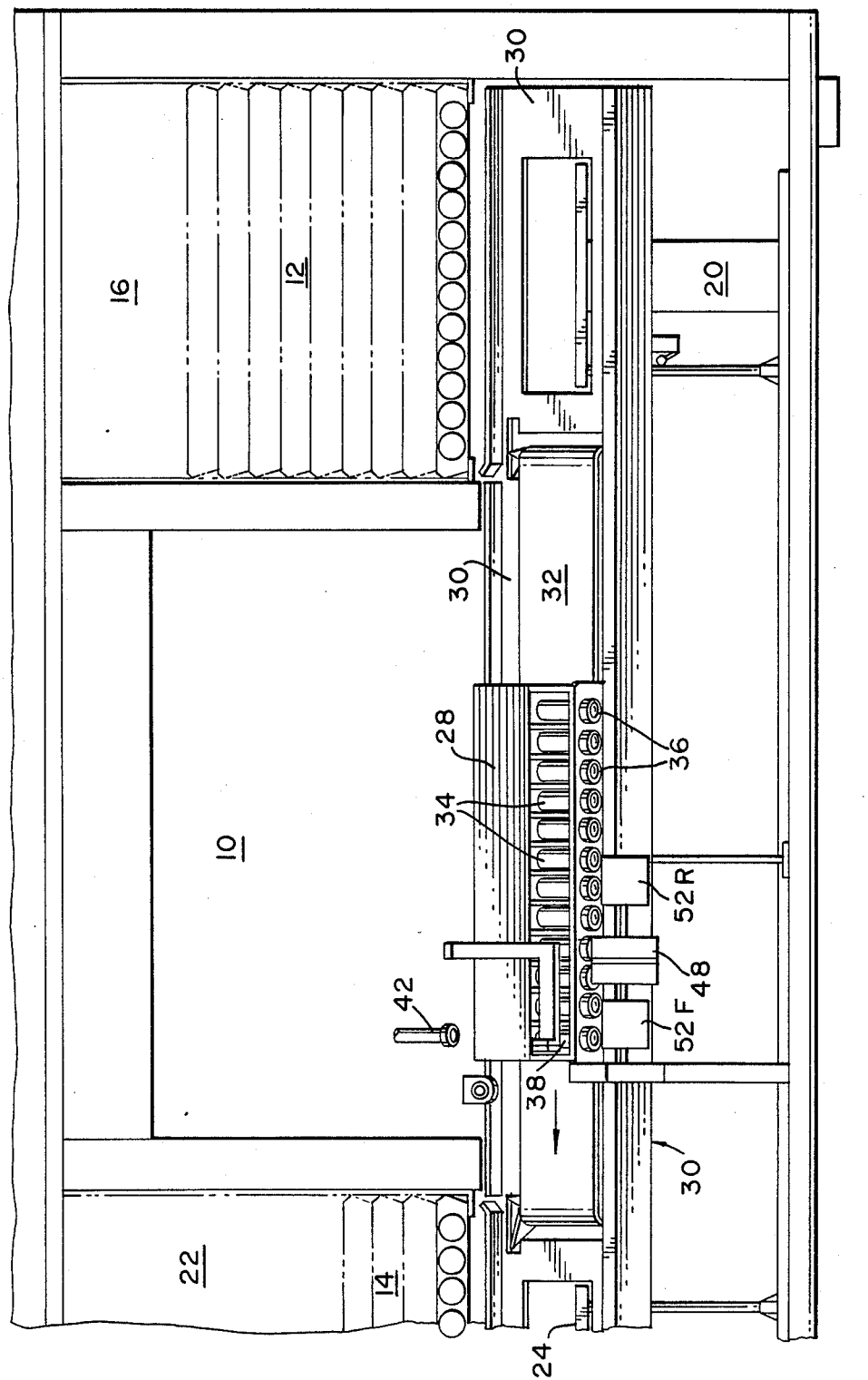
FIG. 2 is a front-elevational view of a major portion of the apparatus of FIG. 1 illustrating the bubble/blood detector of the present invention.

As viewed in FIGS. 1 and 2, the right side of the analyzer 10 is considered to be the sample tube carrier input side and the left side of the analyzer is considered to be the tube carrier output side. For ease of illustration and interpretation, the stacks 12 and 14 of cassettes, carriers, or racks are shown only in FIG. 2, not in FIG. 1. The input stack of racks or carriers 12 is in an input compartment 16 at the base of which is a platform 18 of an elevator mechanism 20. The output side of the system has a similar compartment 22, platform 24, and elevator mechanism 26. After the input side elevator 20 strips a carrier 28 from the bottom of the input stack, that carrier is stepped leftward along a transporting and mixing table 30. The top of the table supports a conveyor belt 32 and there is more than sufficient friction between the bottom surface of the tube rack 28 and the belt 32 to accomplish leftward stepping of the rack 28, each step being approximately the distance between the axial centers of the sealed sample tubes 34 in the rack.

Alignment of a first sample tube 38 and each subsequent tube with an aspiration station 40 can be verified by a sensor 41. When that alignment is achieved, as shown in FIG. 2, a push rod 42 will push upon the bottom end of the sample tube, through an opening in the rack 28, and advance the tube partly out from the rack so that its stopper or sealed end 36 abuts a stripper bar 44. If an aspiration probe tip 46 then also is aligned with the axis of the sample tube, the advancing by the push rod 42 will drive the sealed end 36 onto the probe tip, for penetration through the stopper. The aspiration probe is coupled to a novel photo-optical sensing member (now to be described in detail) and by another length of tubing to the input of the sample segmenting and diluting valve 48, several forms of which are well known and one embodiment is taught in U.S. Pat. No. 4,152,391. Aspirated sample thereupon is processed by the components in the main portion of the hematology analyzer 10 to attain multiparameter blood data. After sample aspiration from the first tube 38, the stripper bar 44 is driven toward the rear, to return the sample tube 38 back into its normal position in the rack 28. Such tube movement strips the seal 36 from the probe tip 46. As well known in the art, the Probe tip and the diluting valve then can be backflushed to eliminate the problem of sample carryover. Thereupon, the transport table will be advanced and rocked to present the next tube to the aspiration station 40 and the aligned push rod 42.

As seen most clearly in the highly schematic view of FIG. 2A, the sample segmenting and diluting valve 48 has been adapted to interconnect, through short lengths of piping or tubing, 50F and 50R to two individual, though substantially identically constructed, photo-optical sensing devices. These members are further identified and characterized as a front sensor 52F and a rear sensor 52R, respectively, due to their obvious placement before and after the segmenting valve 48. The purpose of these two sensing members will become clear as the present description proceeds. A third flexible tube or pipe 55 connects an aspirating pump 120 to the system via the rear sensor 52R. The sensing members, the segmenting valve, and the aspiration probe are adapted to be "back flushed" with clean diluent after each aspirated sample by means of the diluent reservoir 51, pump 53, and valve 57 into a waste receptacle not otherwise identified.

Sensors 52F and 52R are illustrated in more detail in FIGS. 3A-3F. The general configuration of each sensor is cubicle. However, this shape is not to be considered as limiting, since other shapes could be employed.

Figure 3:
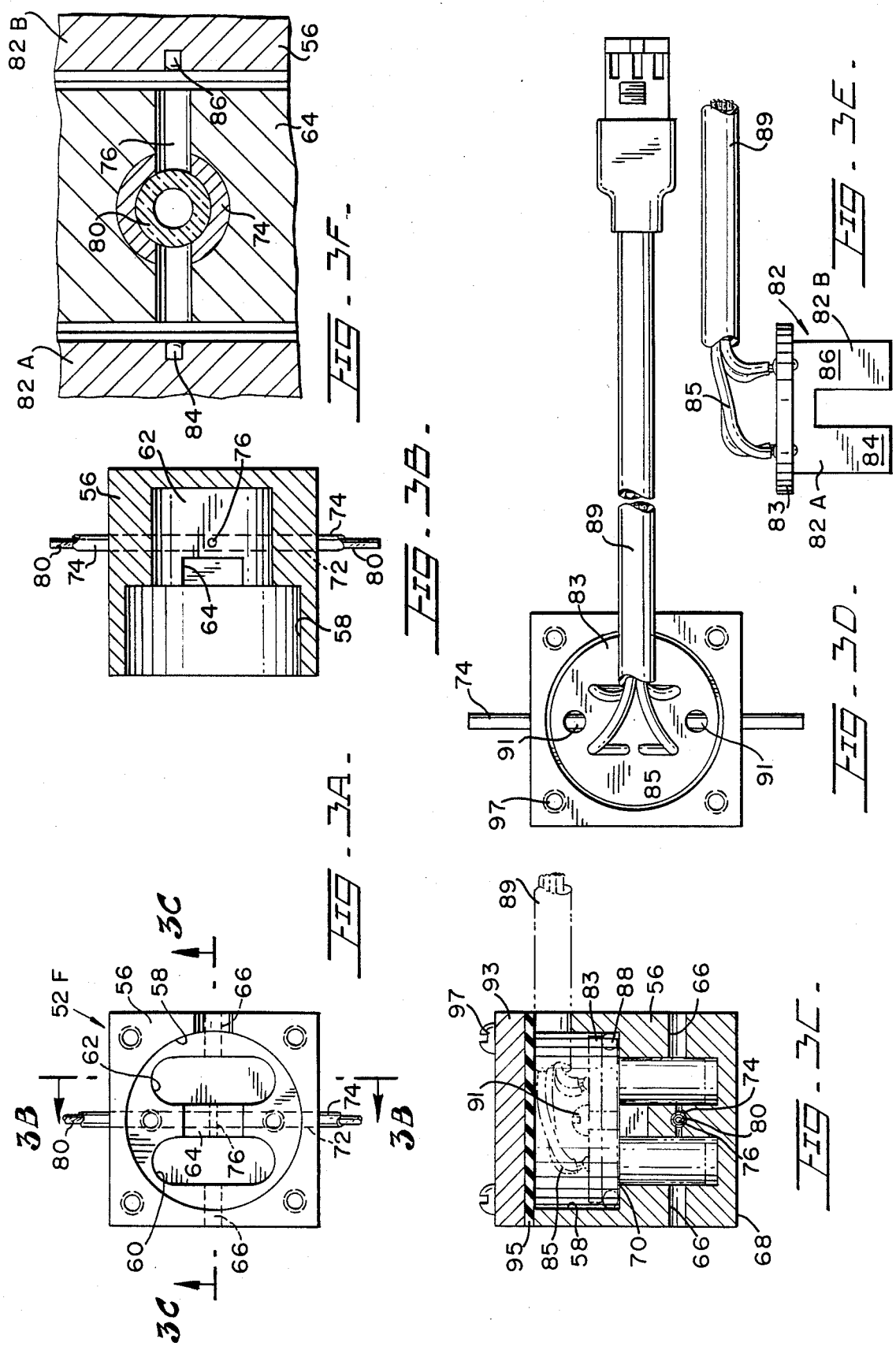
FIG. 3A is a top plan view of the supporting assembly for the photo-optical sensor of the present invention.
FIG. 3B is a sectional view along the line 3B—3B of FIG. 3A.
FIG. 3C is a sectional, side-elevational view along the line 3C—3C of FIG. 3.
FIG. 3D is a top plan view of the assembled sensor illustrating the connecting hardware used therewith.
FIG. 3E is a pictorial view of the sensor assembly and printed circuit board.
FIG. 3F is a greatly enlarged sectional view of the active area of the sensor assembly.

Each sensor member, 52F and 52R, is an infrared responsive device and is seen with reference to FIG. 3A to comprise a block of rigid, opaque material. Each sensor is adapted to detect changes in fluid density, i.e., opacity, of the fluids flowing therethrough. This requires that the sensing units respond to subtle changes in light level. The sensor thus must be free from extraneous surrounding or reflecting light. To this end, a rigid cube or block 56 of material (substantially impervious to the passage of light therethrough) is bored, machined, cast, molded, or otherwise formed to provide a fairly deep, well-like central opening 58 therein from which two substantially parallel additional lozenge-shaped, receptacle-like openings 60 and 62 extend downwardly well into the body of the block 56. A vertical wall member 64, separating the two parallel openings 60 and 62, is provided as a result of the casting or drilling operation.

First horizontal through holes 66 are drilled or formed through opposite sides of the block 56 approximately midway between its bottom 68 (FIG. 3C) and the top 70 of the parallel, lozenge-shaped openings 60 and 62. A second horizontal through hole 72 extends into and through block 56 perpendicular or at right angles to the holes 66, for purposes to be described shortly. A stainless steel tube 74 is Pressed into and through the hole 72, providing a rigid attachment fitting extending from both sides of member 56. Utilizing the manufacturing holes 66 for drill access, a hole 76 of relatively small diameter (0.019 in.) is drilled through the central wall member 64 and through the stainless steel tube 74. A close fitting length of transparent rigid material, e.g., glass tubing 80 (i.d. 0.019 in.), is inserted into and through the stainless steel tube 74 (i.d. 0.042 in.), and is secured to it with suitable cement or bonding agent.

As seen in FIG. 3E, the actual sensing device comprises a unitary yoke or U-shaped assembly member 82 including a light generating element 84 in one leg 82A thereof and a light receiving element 86 in the opposite leg 82B of the yoke 82. A commercial unitary assembly fabricated by Clairex Electronics, 560 S. 3rd Ave., Mt. Vernon, N.Y. 10550 fulfills these requirements. A circular printed circuit board 83 provides a support and acts as an attachment member for the electrical leads 85 of the sensor assembly 82. The two legs 82A and 82B of the yoke 82 are first receivable within the larger receptacle opening 58 in block 56 and are thereafter placed into respective lozenge-shaped receptacles 60 and 62 in close fitting relationship with wall member 64, so that the optical axis of the sensing elements are aligned in close proximity to the actual center of hole 76, as seen in FIG. 3C. The printed circuit board member 83 is assembled to the top of the structure with a sealing O-ring 88 therebetween and acts in the nature of a height adjusting means for the active sensing elements of the assembly, and also as means for attaching the wires (cable 89) that carry the electrical signals to and from the circuit configuration of FIG. 4.

Because the detection mechanism of the present invention is adapted to detect occluding material on the order of 0.060 microliter in size, (depending on blood value), the maximum size bubble which can exist within the optical axis is a function of the structural configuration of the hardware employed in the system. It is essential to the efficient operation of the apparatus that the sensing mechanism be oriented with critical exactness to accommodate the device to this precision.

The light sensing assembly is accurately oriented within the block 56 so that the axial centers thereof are aligned with the center of the "window" 76 thus guaranteeing that the light will pass through the window 76 with minimum loss due to the tolerance of the associated parts of the assembly. The printed circuit board member 83 and the O-ring 88 provide means for adjusting the vertical positioning of the sensor assembly by screwing the two adjusting screws 91 against the O-ring 88, effectively aligning the two sensing elements 84 and 86 with respect to the light passing window, thus assuring that the light from the generating element is accurately directed to the light receiving element. This is considered to be a device adjustment and is performed as a preliminary setup of the system. So as to seal the interior of the sensor assembly against the ingress of moisture, dirt, etc., a cover member 93 is secured by screws 97 to the block 56 over a sealing gasket 95.

2. Operational Description

Figure 4:
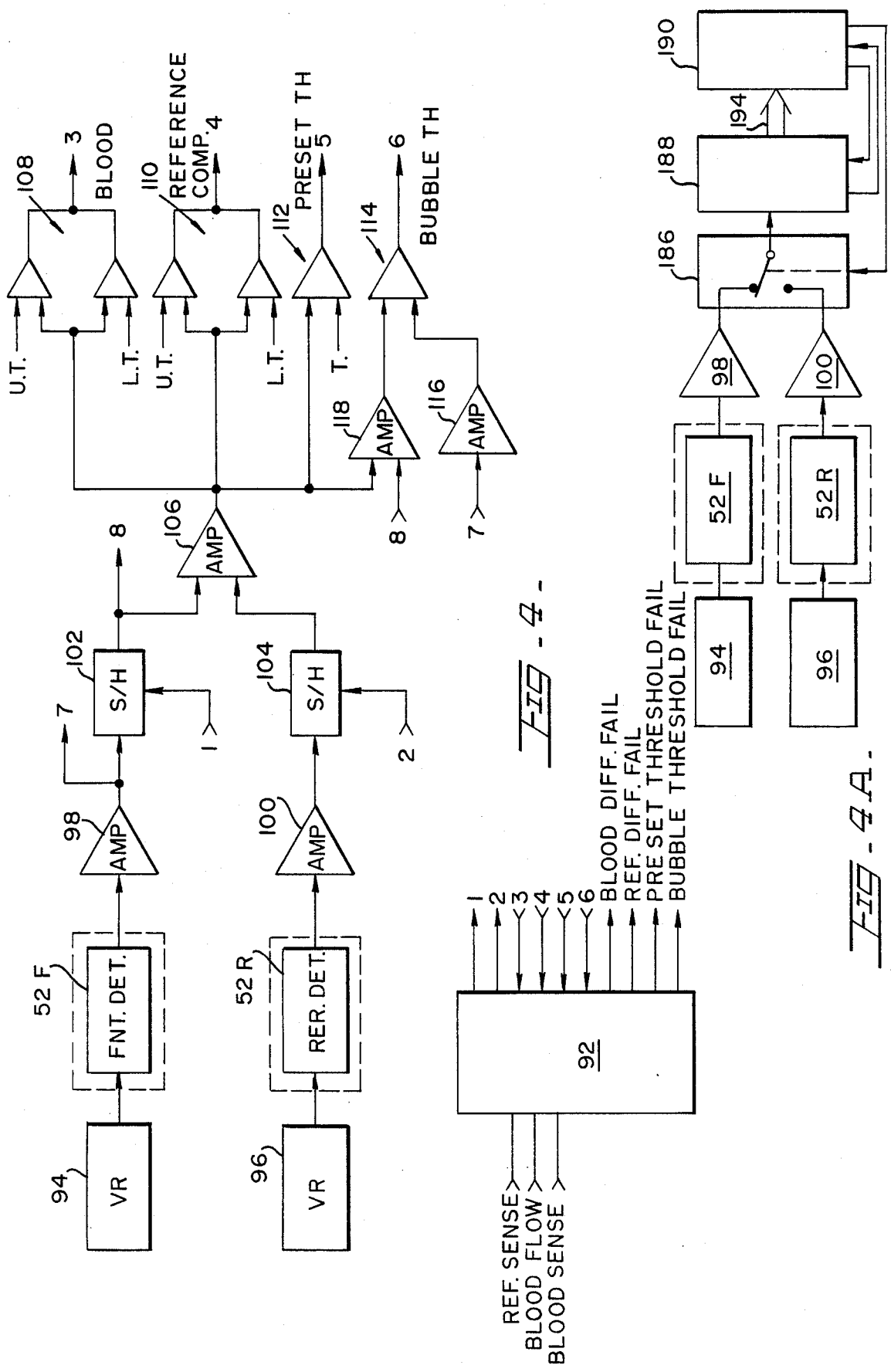
FIG. 4 is a block diagram of the bubble/blood detector apparatus of the present invention.
Figure 5:
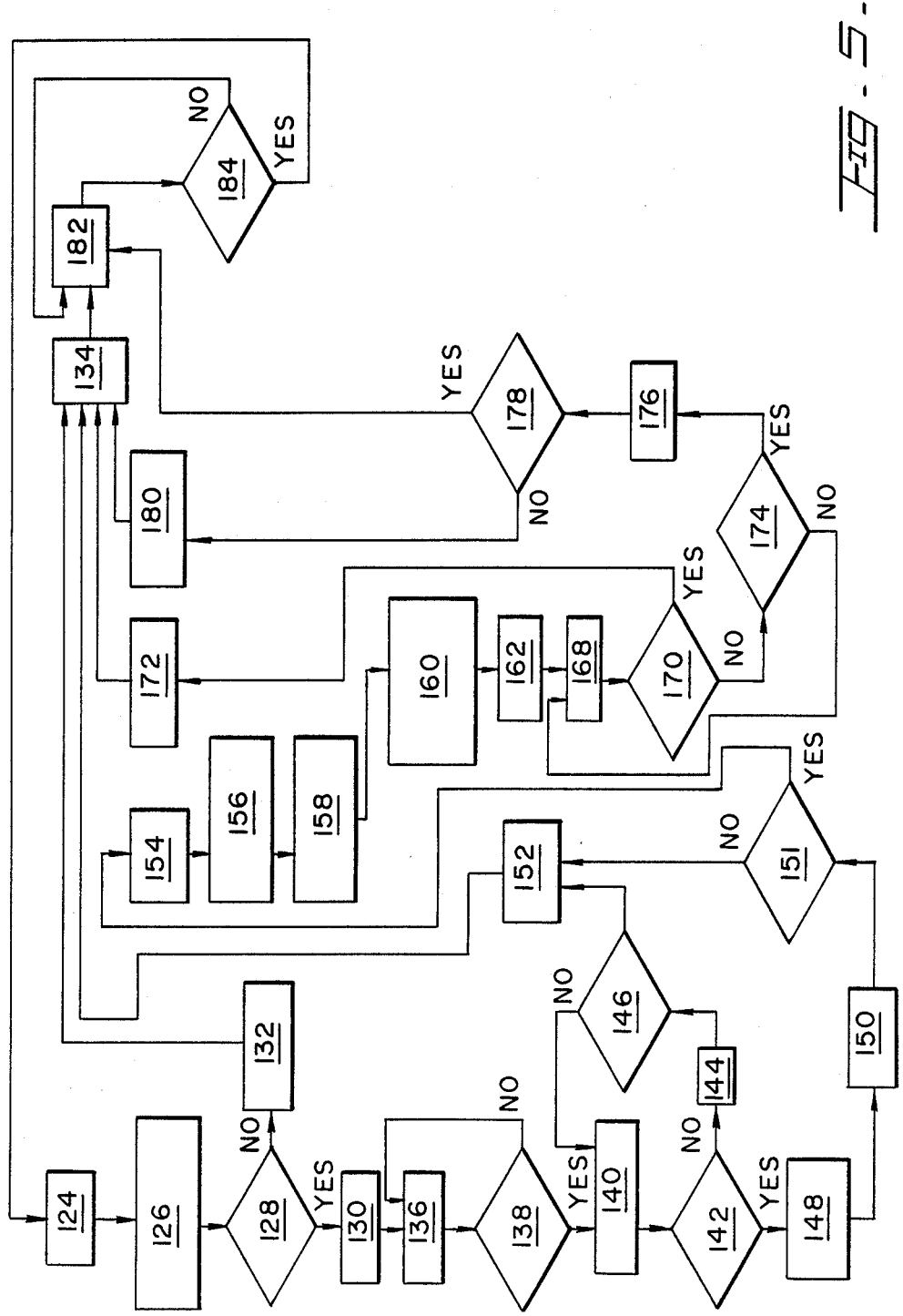
FIG. 5 is a flow chart for a computer controlled system utilizing the present invention.
Figure 6:
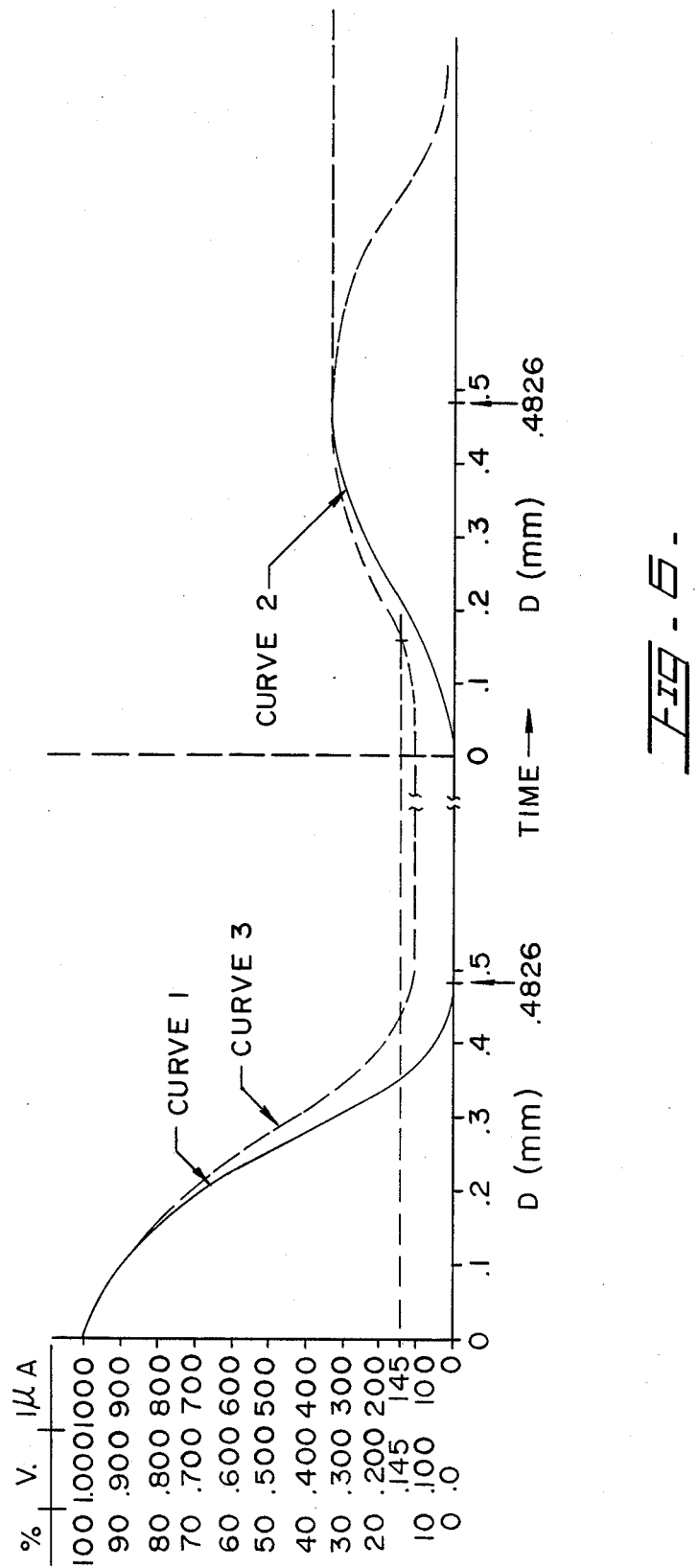
FIG. 6 is an idealized, highly schematic curve for the front sensor of the bubble/blood detector of the present invention.

The operation of the present invention is set forth herein with respect to (1) the block diagram of FIG. 4, (2) the flow diagram of FIG. 5, and (3) the idealized curve of FIG. 6. At the beginning of each cycle of operation, it should be noted that the previous material sample is flushed from the system with clean diluent-electrolyte and the two sensors are "looking" through diluent.

In the block diagram of FIG. 4A, it is seen that a control system 92, also sometimes referred to as the "state controller" includes among other portions of the apparatus, the inputs labeled "Reference Sense", "Blood Flow", and "Blood Sense" from the main system hardware-software (not shown herein). Also included in the control system are clock pulse generation circuits, all logic, delay circuits, latches, and assorted buffers used therein.

A brief general functional description of the controller 92 and logic operation is as follows:

1. The "Reference Sense" signal going high causes the state controller to go to State ∅. All the latches are cleared and the sample and hold circuits are set to the sample mode.

2. The state controller advances directly to State 1, where it waits on the "Blood Flow" signal to go high. While at State 1, the diluent difference signal on the front and rear sensor is checked.

3. When "Blood Flow" goes high, the diluent level signal on the rear sensor is held by the rear sample and hold circuit. The controller is allowed to go to State 2. As the blood moves past the front sensor, the difference between the held diluent level signal on the rear sample and hold circuit and the blood signal on the front sensor is monitored. When the difference is greater that a preset level, determined by the system's upper blood limit, a time delay circuit is energized and, at the end of the time delay, the blood value signal on the front sensor is held by the front sample and hold circuit, and the controller is allowed to step to State 3.

4. At State 3, the bubble threshold level is energized for the duration of the blood movement. The bubble threshol level is established by adding the held blood value on the front sample and hold circuit to 5% of the difference of the held diluent value on the rear sensor and the held blood value on the front sensor. The bubble signal level threshold = Blood + 5%(Diluent-Blood). Also, the difference between diluent and blood must remain below the preset threshold level. The controller waits at State 3 for the "Blood Sense" signal.

5. When the "Blood Sense" signal arrives, the controller is allowed to step through States 4 and 5 and stops at State 6, where it waits on the "Reference Sense" signal to start another cycle. When the controller steps to State 4, the front and rear sample and hold circuits are switched back to sample mode and the blood levels on the front and rear sensors are sampled. The controller steps to State 5 where the blood value on the front sensor is compared to the blood value on the rear sensor. The controller steps to State 6 where it waits on the "Diluent Sense" signal to start another cycle.

The segmenting and sampling valve now is accuated approximately the same time as the blood sense signal, and the aliquot of whole blood is segmented by the valve and sent to the blood testing baths for further handling by the COULTER COUNTER ® apparatus.

Both an audible alarm as well as a printed record of the various aspects of the blood/bubble detection activity is produced by the apparatus, effectively enabling an operator to easily and quickly monitor and/or identify any blood sample which the testing indicates might be inaccurate or faulty.

The outputs to the main system are: "Blood difference fail", "Reference difference fail", "Preset threshold fail", and "Bubble threshold fail"; each of these conditions are further described later on herein. The control system is capable of acting in at least seven different although related modes or states which will be referred to later on herein.

At the beginning of any cycle of operation of the present invention, certain parameter-conditions or states of the apparatus, are preset and all control system registers are clear. The state controller waits for the first signal input to start the bubble detection sequence or operation, after which the controller steps through successive states controlling the logic and comparison functions of the system.

The sensor members 52F and 52R, as before mentioned, are infrared type electro-optical units and are used to sense the change in density (opacity) of the fluid passed therethrough. As between blood, air, and the electrolyte-diluent, diluent, in this system, produces the highest signal output from the sensor (light detector). The diluent signal level is employed herein as a standard reference signal level against which all other signal levels are compared when they are subsequently developed. As noted in the curve of FIG. 6, diluent signal level is characterized as the 100% level. This would be the condition with diluent completely covering the active area—the window—of the sensors, i.e., the aperture 76.

Initially, the two sensors 52F and 52R are preset to the same 1 volt signal level output by adjusting the respective adjustable feedback voltage regulators 94 and 96 which supply current to the light emitters 84. This 1 volt signal is characterized as the 100% reference level for subsequent comparisons. Briefly, the 1 volt signals generated by the respective infrared sensors are first fed to respective ×10 amplifiers 98 and 100 where they are scaled up by 10 times. The output from the amplifiers 98 and 100 then is sent to a respective front or rear sample and hold circuit 102 and 104. From each sample and hold circuit, the respective signal is fed to a difference amplifier 106, from which point the signal goes to a respective comparator circuit 108, 110, 112, or 114. One output from the amplifier 98 is sent to an inverter amplifier 116 and then to the comparator 114. The output of the front sample and hold circuit 102 also is fed to an adder amplifier 118 and the adder output goes to the comparator 114, as will be explained hereinafter.

With diluent from the previous cycle of operation in the system, sensors 52F and 52R should be outputting identical signal reference levels, in which case the difference amplifier 106 output is zero "0" and the reference difference comparator 110 sees no difference. However, actual signal outputs from 52F and 52R can in fact vary slightly with respect to one another, but so long as the variation is within a specified limit, e.g., ±7%, the variation is ignored.

Three signals are sent from the analyzer controller to controller 92 at different times. The first is "diluent sense". This signal causes the comparison of the diluent normally in the tubing on both sides of the sample valve. The diluent is used as a reference level, as earlier described, since diluent produces the largest signal output. This is characterized as the 100% or 1 volt level (FIG. 6), and both sensors should have a 1 volt signal output at this stage, assuming that both sensors see 100% diluent.

Next, the "blood flow" signal is input to the controller 92 at the same time that the pump 120 aspirates the whole blood from the sample tube 38 into the system via aspirator needle 46. At this time, the diluent value signal is "held" by means of the rear sample and hold circuit 104. This establishes a diluent reference level to compare against as blood comes through into the front sensor 52F. It is noted that as blood now comes into the system behind the diluent, the blood is not yet well defined, since the leading edge of the blood is or may be diffused by the diluent ahead of it.

During this time, the signal value of the front sensor 52F is substracted by the difference amplifier 106 from the stored and held signal value of the rear sensor 52R. When the preset level (0.20 volts on a 1 volt scale) is reached, a determination is made that the upper range has been attained. As shown in the curve of FIG. 6, this can be characterized as 20% up from "0" or 80% down from the diluent reference level. A fixed time delay of 225 ms (milliseconds) is set before taking the blood value to assure that clean blood, and only blood with no contaminants, is now within the system. Basically, this delay is employed to permit the blood to have sufficient time to well establish its particular level within the blood range and be void of any contaminants such as diluent or air. At the end of the 225 ms delay, the signal level value on the front sensor 52F is held in the front sample and hold circuit 102. This signal will be at or below the 0.20 volt level, but normally considerably below this value.

The logic of the control circuit 92 is arranged so that the signal cannot go back above this 0.2 volt level without being detected. If, however, it should go above this value during the cycle, this indicates an error, and it is flagged.

During the aspiration time, as the blood passes into and through the front sensor, it is checked as to signal level. If the 80% down level, earlier referred to, is not reached, an error is indicated, when the "blood flow" signal goes away. This error would be indicative of several conditions, such as: (1) the blood was out of the measurement range of the system; (2) a tube of air or a tube of diluent was put in the analyzer instead of blood; (3) the sample valve 48 did not actuate (rotate) properly, so the previous blood sample was not flushed out and left the previous blood in the system; (4) either the front, rear, or both sensors are disconnected or defective; (5) a partial amount of the aspirated material entered the system, but was not of sufficient quantity to keep the signal value below the threshold.

A bubble threshold value now is established as a means of detecting any foreign material, such as bubbles, in the blood. To the signal value developed by the front sensor 52F, which is now stored in the front sample and hold circuit 102, is added by the adder amplifier 118, a portion, i.e., a percentage, of the difference between the diluent value stored in the rear sample and hold circuit 104 and the stored-held blood value on the front sample and hold 102. This signal level or value is called the bubble threshold. The bubble threshold value is a variable. It varies with each blood sample. This bubble threshold is established always to be above the blood level value of the particular blood in the system. While this value is set, the blood continues to flow within the system, until the required or preset volume has been aspirated by the pump 120. Anytime that the front sensor signal value goes above the set threshold value, a flag will be set, indicating contaminants in the blood.

The next signal from the stacker-analyzer controller to the control circuit 92 is the "blood sense" signal. During this time, blood should have moved into and through the system sufficiently far so that blood completely covers the front sensor 52F through the valve 48 and the rear sensor 52R and should be free of dilution from diluent. At this point in time, the signals from both sensors should be identical.

When the "blood sense" signal is received from the analyzer controller, the system control circuit 92, reactivates the two sample and hold circuits 102 and 104, which permits the signals from the sensors 52F and 52R (which should both be blood signals) to pass into the differential amplifier 106. The blood signals provided by the respective front and rear sensors 52F and 52R now are compared. These two signals must be within a fixed preset value ($\pm 1\%$) of each other, or conversely they could be identical with pure blood with no contaminants, such as diluent. If the difference between the two signals exceeds the so-called difference "window" via the blood comparator 112, this error is flagged indicating contaminants or that the blood volume was not sufficient to reach the rear sensor 52R. The controller then steps to its final state and the cycle is completed.

The circuit then waits for the next cycle and the diluent electrolyte sense comparison signal ("reference sense") to come in to the control circuit apparatus 92, as before.

During the cycle, if: the initial reference diluent levels have separated by some percent above or below the set percentage; if the preset threshold is not reached or it is reached, but did not stay below the level; if a bubble develops that makes the front sensor signal greater than the bubble threshold; or if the blood sense signal level does not satisfy its set limits at the end of the cycle; an error is reported for any of these conditions and a so-called "flag" is set and the operator is signalled accordingly.

The curve of FIG. 6 illustrates an idealized, pictorial representation of electrolyte-diluent reference level on the front sensor 52F, illustrating a frontal wave of blood as the blood crosses the detection area and arrives at a time where there is total blood occluding the detector area of the sensor 52F. "D" represents the distance the blood edge moves as it crosses the detector area.

The vertical axis of the graph is divided into three parts: (1) the percentage of diluent; (2) the voltage developed by the detector; and (3) the current in microamps. As the leading edge of blood (curve 1) traverses the diameter of the front sensor stated as 0.4826 mm (or 0.019 in), i.e., the detector area, the current level changes as shown. The horizontal axis of the graph also represents both the elapsed time for the conditions specified in the graph, as well as the change in detector area being covered by the fluid, i.e., 0.0 to 0.5 mm.

As the leading edge of blood enters the circular area of the detector 52F, starts at "0", and proceeds through it, the current, as can be seen, starts diminishing in value, since less and less light is able to penetrate to the detector. Ideally if the blood completely blocked all the light to the detector, this would produce a "0" current output. Since the blood level is not well defined when it enters the 80% level, because it may have diluent mixed with it, the 225 ms delay allows enough time for blood to attain its own level free of any contaminants. Assuming (some time subsequent to the end of the delay) that a bubble does enter the system then, as depicted in curve 2 of FIG. 6 starting at "0", the bubble crosses the detector area as did the blood and the current output from the detector immediately rises to a maximum (at point 0.4826 mm) as illustrated in curve 2. This condition is promptly flagged to alert the operator to the error.

If the bubble exceeds the diameter of the detector area (right of FIG. 6), for example, if the bubble were longer than the diameter of the detector area, the current output from the detector would remain high as seen along the upper dashed line, to the right in FIG. 6 until the bubble had diminished in size-length and blood once again is detected.

An example of circuit operation in detecting a bubble with nominal voltage values is now set forth, with reference to curve 3. Assume that the front sensor signal output reaches the 80% down level. The delay of 225 milliseconds is initiated. At the end of the delay, the blood value is held at 100 microamps or 0.1 volt. To this value is now added a percentage of the difference between the reference value (diluent-electrolyte) which is 1000 microamps minus 100 (the blood level value) or 900 microamps. This value 900 microamps is multiplied times the percentage factor which in this case would be 5% (an empirically derived tolerance-sensitivity figure) to produce 45 microamps. At this point, therefore, the bubble threshold is equal to 100 microamps, the blood level, plus 45 microamps, which is 5% of the 900 microamps or 145 microamps. Therefore, if the signal output on the front sensor 52F goes back above the 145 microamps level, there is an air bubble in the system and this condition is flagged to the operator.

Alternately, the system previously described can be implemented, as in FIG. 4A, using a computer, for example, to provide control functions, mathematical computations, quality checks, etc. As implemented by the software of the system stacker-analyzer computer, the flow diagram of FIG. 5 relates back to the block diagram of FIG. 4A. As previously noted herein, at the beginning of any cycle 124 (corresponding to the arrival of the "diluent sense" signal), both sensors 52F and 52R are "looking through" diluent-electrolyte. The two sensor outputs are set to be identical. This is the earlier referred to 100% level. Two sensor outputs are compared against each other and must meet a preset threshold value previously fixed in the system electronics. The two outputs may move apart by a percentage previously determined.

The analog to digital values of the front and rear sensors are now read as indicated at 126 FIG. 5. These are the diluent values. The computer software next checks whether the difference between the front and rear sensors is less than the maximum acceptable value 128. If it is, then the value is stored 130. If it is not, then an error flag is set, indicated at 132, and this condition is reported, i.e., recorded, as a failed condition 134.

The next step is the "blood flow" signal 136. The system waits for the "blood flow" signal to come 138. If it does not, the wait continues until the signal is received. When the signal is received, the software continually reads the A to D value of the front sensor 140. If this signal value is 80% lower than the stored value of the rear sensor 142, then the program continues. If it is not, a short delay 144 is set and the system checks to see if the "blood flow" signal has gone away. If "blood flow" has gone away, an error flag is set (152) and reported at 134. If "blood flow" has not gone away, the loop continues until it does.

If the blood reaches the 80% down level (earlier referred to herein), a delay 148 is set of 225 milliseconds, which is considered to be sufficient time for the diluent-blood interface to pass and for the blood to reach the level determined by its own characteristics free of any contaminants. However, when the aspirate signal terminates and if the 80% down level was never reached, an error flag 152 is set and the condition is reported at 134.

At the end of the 225 millisecond delay, the software reads the A/D value of the front sensor 150. The electronics then looks to see if the stored value is still 80% lower than the stored value of the rear sensor 151. If it goes above the 20% level or the 80% down level, an error flag is set 152 and the condition is reported at 134. If it is at or below the 80% down level (0.2 volts), the value of the front sensor is stored 154. At this point, both the blood value on 52F and the diluent rear value on 52R are held (stored).

The computer software now subtracts the stored front sensor value from the stored rear sensor value. This is the diluent value minus the blood value 156. The diluent minus blood value is multiplied by 5% (158). This result is added to the stored front sensor value 160. (This is the blood value plus 5% of the difference between the diluent and blood.) This value becomes the bubble threshold value which is stored at 162. The blood is still moving through the system at the time.

The signal level value of the front sensor is read next 168. The software determines if the value of the front sensor is greater than the bubble threshold 170. If it is, an error flag indicating a detected bubble is set 172 and an error is indicated at 134. If it is not, the system software looks for the "blood sense" signal to arrive 174. If the "blood sense" signal has not arrived, then the software loops back to the front sensor 168 and reads the signal level again. This loop continues until the "blood sense" signal arrives. If on the other hand, the "blood sense" signal has arrived, then the value of the rear sensor is read 176.

The system software next determines the difference between the value of the front sensor and the value just read from the rear sensor and looks to see whether this result is less than the maximum acceptable signal level value 178. If it is not, an error flag is set 180 indicating that the blood is not the same at the front and rear sensors. This error is reported and indicated at 134.

If the result is less than the maximum acceptable value level, the cycle is finished and the system waits for the next cycle command 182. A new command 184 starts the detection system for the next cycle.

By adding a computer facility interface to the apparatus illustrated in FIG. 4, the bubble detection system can be expanded as illustrated in FIG. 4A. For example, quality control means for monitoring the drift on the front and rear sensors can be provided, all of the comparisons previously referred to can be performed easily, swiftly and accurately. The sensitivity of the front to rear sensor difference can be measurably enhanced and improved among other capabilities made available by this improvement.

FIG. 4A illustrates in block diagram form the additional elements of the combination. As noted therein, the outputs from amplifiers 98 and 100 are first fed to an analog switch 186, which acts in the nature of a high speed switching device, so that the signal outputs can be switched automatically from the front sensor channel 52F to the rear sensor channel 52R. The selected output from analog switch 186 is fed to an analog to digital converter 188 which converts the incoming selected analog signal to digital form for application to computer system 190.

The system 190 determines which channel it desires to look at and it closes analog switch 186. This signal comes through into the A/D converter 188. The computer 190 has the A/D conversion performed by the A/D, and the A/D sends to the computer an end of conversion signal. The computer 190 takes the data on bus 194, i.e., the digital values and performs the required functions as set forth in the flow diagram of FIG. 5.

Although a specific embodiment has been illustrated and described, it should be obvious to those skilled in the art that certain changes and modifications may be made therein without departing from the invention in its broader aspects, and, therefore, the aim in the appended claims is to cover all such changes and modifications as fall within the true spirit and scope of the invention.

What is claimed is:

1. An electronic fluid monitoring system wherein liquid material is moved into and through apparatus for detecting and indicating to an operator or to an output monitoring device the presence or absence of air emboli or other unwanted contaminants therein comprising:

control logic means including means for initiating and applying various signal voltage levels to said apparatus which levels are developed during operation thereof and for receiving and processing signal voltage levels applied thereto;

liquid material processing means of segmenting a fixed volume of liquid from the liquid flowing through said processing means for subsequent handling and testing, said processing means having an input and an output area;

first sensing means for sensing the liquid at said input area of said processing means and for developing a first status voltage signal level respecting the status of said liquid in said sensing means;

second sensing means for sensing the liquid at said output area of said processing means and for developing a second status voltage signal level respecting the status of said liquid in said sensing means;

means for sampling and storing the signal developed by said first and second sensing means;

means operably associated with said control logic means for comparing the signals from said first and said second sensing means for developing a difference signal as a result of said comparison, and means for producing a visual and audible indication of the result of the comparison; and means establishing a preset threshold signal level against which the difference signal developed as a result of the comparison of said first and second sensing signals is compared, said threshold signal level in conjunction with said control logic means, being effective to accept said liquid material status signals if said difference signal is at or below said preset threshold level, and to reject said liquid material status signals of said difference signal is above said threshold level.

2. The invention in accordance with claim 1 wherein said control logic means comprises a multistate electronic circuit device.

3. The invention in accordance with claim 1 wherein said liquid material processing means comprises a rotatable sample and segmenting valve having an input orifice, an output orifice, and means for ejecting a segmented sample therefrom.

4. The invention in accordance with claim 3 wherein said first and second sensing means comprise photooptical members including means for interconnecting said members to said sampling and segmenting valve.

5. The invention in accordance with claim 4 wherein each said sensing means includes infrared optical radiation generating and receiving means.

6. The invention in accordance with claim 3 wherein said first sensing means is coupled to said input orifice of said valve and said second sensing means is coupled to said output orifice of said valve and wherein a highly light transmissive material first is passed into and through both said sensing means and said valve, so as to establish reference signal level outputs from both said sensing means for comparison with a liquid material subsequently passed into and through said sensing means and said value within which it is desired to detect the presence of air emboli and other contaminants.

7. The invention in accordance with claim 1 further including means for adjusting and controlling the signal level output of said sensing means, effective to establish a base reference level signal related to the opacity or density of the liquid passed therethrough.

8. The invention in accordance with claim 1 further including means in said control logic means for providing output control signals indicating that the signals from the first and second sensing means were different, or that the preset threshold level signal was not exceeded, or that an air emboli or other contaminant was detected during operation of the apparatus.

9. The invention in accordance with claim 1 wherein each said sensing means further comprise an opaque member provided with an orifice therein of 0.019 inch diameter, and wherein each said sensing means is adapted to straddle said flowing fluid.

10. The invention in accordance with claim 1 wherein said means for sampling and storing is coupled to respective first and second sensing means and wherein the signal output from said means for sampling and storing is fed to a difference amplifier for extracting the difference output between said first and second sensing means signals in response to the presence of fluid to be tested therein, and wherein the difference output signal is compared by a selected comparator circuit to determine the status of the fluid and the presence or absence of contaminants in the system.

11. The method of testing for and detecting contaminants such as air emboli in a fluid monitoring system, wherein fluid is passed into and through oppositely disposed signal generating sensing members disposed on opposite respective sides of a fluid processing station and wherein a diluent of highly light transmissive material is introduced into the system to establish a reference standard signal level, said method comprising the steps of:

comparing the signals sensed from the diluent by said sensing members;

aspirating fluid to be tested into the system, while storing the diluent signal from one of said sensing members;

establishing a comparison signal level for said fluid to be tested;

subtracting the signal value of the aspirated fluid to be tested from the stored diluent signal value derived from the diluent;

storing the signal value derived by the sensing member in response to the aspiration of fluid;

establishing a contaminant threshold value by adding to the stored signal value from the aspiration step a portion of the difference between the stored diluent signal value and the stored signal value derived by the said sensing members as a result of the aspiration step; and indicating either failed or passed conditions signifying the presence or absence, respectively, of contaminants such as air emboli in the system.

* * * * *

UNITED STATES PATENT AND TRADEMARK OFFICE
CERTIFICATE OF CORRECTION

PATENT NO. : 4,752,690

DATED : June 21, 1988

INVENTOR(S) : Bobby D. James

It is certified that error appears in the above—identified patent and that said Letters Patent is hereby corrected as shown below:

```
Column 5, line 17, change "Probe" to --probe--;
Column 6, line 1, change "Pressed" to --pressed--;
Column 7, line 29, change "that" to --than--;
Column 7, line 38, change "threshol" to --threshold--;
Column 13, line 33, change "of" to --for--;
Column 13, line 62, change "of" to --if--.
```

Signed and Sealed this

Ninth Day of July, 1991

Attest:

HARRY F. MANBECK, JR.

*Attesting Officer*   *Commissioner of Patents and Trademarks*